United States Patent [19]

Masilamani et al.

[11] 4,410,705

[45] Oct. 18, 1983

[54] NOVEL SPIRO OXAZOLINE COMPOUNDS AND METHODS FOR THEIR PREPARATION AND USE

[75] Inventors: Divakaran Masilamani, Morristown; Edward H. Manahan, Morris Plains, both of N.J.

[73] Assignee: Allied Corporation, Morris Township, Morris County, N.J.

[21] Appl. No.: 298,050

[22] Filed: Aug. 31, 1981

[51] Int. Cl.$^3$ .................... C07D 498/00; A61K 31/42
[52] U.S. Cl. ................................ 548/216; 260/438.1; 260/464; 424/272; 568/305; 568/306; 568/309; 568/329; 568/330; 568/338; 568/375; 568/376; 568/379; 568/380; 564/258; 564/454; 564/455
[58] Field of Search ......................................... 548/216

[56] References Cited

U.S. PATENT DOCUMENTS

| Re. 92,902 | 2/1979 | Mauvernay et al. | 548/216 |
| 3,193,525 | 7/1965 | Kallert et al. | 260/45.9 |
| 3,382,266 | 5/1968 | Butler | 260/438.1 |
| 3,387,026 | 6/1968 | Chafetz et al. | 260/514 |
| 4,018,827 | 4/1977 | Rao et al. | 260/586 P |

*Primary Examiner*—Donald G. Daus
*Assistant Examiner*—S. A. Gibson
*Attorney, Agent, or Firm*—Kenneth E. Stroup, Jr.; Alan M. Doernberg; Gerhard H. Fuchs

[57] ABSTRACT

A process for preparing substituted or unsubstituted benzoxazoline compound by reacting ammonia, a cycloalkanone and oxygen in the presence of metal cations.

17 Claims, No Drawings

NOVEL SPIRO OXAZOLINE COMPOUNDS AND METHODS FOR THEIR PREPARATION AND USE

BACKGROUND OF THE INVENTION

1. Field of the Invention

This invention relates to novel intermediate compounds, and to methods for their preparation and use as intermediates in the preparation of other useful compounds. More particularly, this invention relates to novel oxazoline compounds, their preparation and methods for using such compounds in the preparation of various cycloalkane-1,2-dione, cycloalkane-1,2-dione oxime and cyclohexane-1,2-dione dioxime derivatives.

2. Brief Description of the Prior Art

It has been reported in the literature that treatment of cycloalkanone compounds with oxygen in the presence of an alkali metal halide catalyst causes ring cleavage and the production of the corresponding ketomonocarboxylic acid. For example, U.S. Pat. No. 3,387,026 describes a procedure in which 2-methyl-cyclohexanone is treated with oxygen gas in the presence of potassium fluoride or lithium fluoride to provide 6-oxoheptanoic acid.

Other prior art has reported that treatment of cycloalkanone compounds with oxygen gas in the presence of an alkali metal hydroxide or alkoxide will provide the corresponding cycloalkane-1,2-dione compound. For example, the references, U.S. Pat. No. 4,018,827, and Rao, Durvasula V, et al., "Base Catalyzed Autoxidation of Cyclic Ketones", J. Org. Chem. vol. 44, No. 3 pp. 456–458, (1979) describe a process in which cyclohexanone is treated with oxygen gas in the presence of potassium butoxide to provide cyclohexanone-1,2-dione. While the above process can be used to prepare cycloalkane-1,2-dione compounds, it suffers from several disadvantages. The reaction yields are relatively low, and vary over a wide range, thus, the process is not very efficient. Furthermore, the process does not appear to be applicable to the preparation of 1,2-dione derivatives of cycloalkanone compounds having more than six ring carbon atoms. For example, Rao, Durvasula V., et al, supra disclose that use of cycloheptanone reactants in the process provides tricyclic compounds having ester and keto functions.

SUMMARY OF THE INVENTION

Surprisingly, we have discovered that certain cycloalkanone compounds when treated with base and oxygen in the presence of a metal catalyst do not form either the corresponding keto acid, cycloalkane-1,2-dione on tricyclic compounds having ester and keto functions, as would be expected from the prior art. Rather, these compounds condense under the reaction conditions of this invention to be described hereinbelow in more detail to provide a stable oxazoline compound in good yields.

In accordance with this invention there is provided a novel oxazoline compound of the formula:

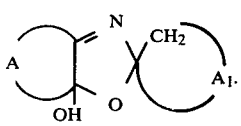

This invention also provides a process for preparing said oxazoline compound comprising reacting a compounds of the formulas or mixture thereof:

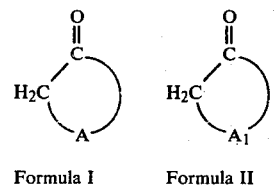

Formula I           Formula II oxygen, and ammonia in the liquid phase in the presence of a catalytically effective amount of a metal catalyst. In the above structural Formulas, "A" and "A₁" are selected such that compounds of Formulas I and II are same or different and are straight or branched alkylene chains having from about 3 to about 15 carbon atoms completing a 5, 6, 7 or 8 membered mono-, bi-, or tricyclic structure. Optionally, "A" and "A₁" may be unsubstituted or substituted with one or more "inert substituents" provided that at least one of the carbon atoms of the compound of Formula I alpha to the keto functional group in the ring is substituted with hydrogen.

As used herein, "inert substituents" are substituents which are inert under the conditions of the reaction, i.e. do not themself enter into the reaction or otherwise interfer in a substantial way with the desired course of the reaction.

The novel oxazoline compounds of this invention are useful as intermediates in the preparation of other useful compounds. For example, the above described oxazoline compound of this invention can be treated with water in the presence of hydrogen ions, H+, to provide corresponding cycloalkane-1,2-dione and cycloalkanone compounds of the formula:

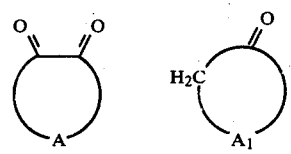

wherein "A" or "A₁" are as described hereinabove. The cycloalkane-1,2-dione compound prepared in accordance with the present invention are well known in the art and are useful as chemical intermediates in a variety of processes. For example, 1,2-cyclohexanedione can be hydrogenated using known procedures, (as for example heating in the presence of a palladium on charcoal catalyst) to yield catechol which is a dihydric phenol well-known to be useful as an antioxidant, photographic chemical and the like. The 1,2-cycloalkanediones are also known to yield dithiosemicarbazides which as disclosed in U.S. Pat. No. 3,382,266, in the form of metal chelates, are useful in the treatment of coccidiosis. The 1,2-cycloalkanediones are also useful, in combination with carbodimides, in the stabilization of polyurethanes against hydrolytic attack in accordance with U.S. Pat. No. 3,193,525.

A number of methods for the preparation of 1,2-cycloalkanediones are known. For example, 1,2-cyclohexanedione has been obtained by brominating cyclohexanone and hydrolyzing the 2,6-dibromocyclohexanone to the corresponding dihydroxycyclohexanone which then loses water to yield the dione; This procedure is described in detail in Wallach et al., Annalen U.S. Pat. No. 437,132, 1924. The 1,2-cyclohexanedione compound has also been obtained by heating divinyl glycol with copper, see for example, Urion, Comptes rendus 192, 1661, 1931 and by oxidizing cyclohexanone with selenium dioxide in ethanolic solution as described in Riley et al. J. Chem. Soc. 1932, 1875. A procedure involving the oxidation of cyclohexanone with selenious acid or selenium dioxide in aqueous dioxane is described in Organic Synthesis, Collective Volume IV, 1963, 229, John Wiley and Sons Inc., New York. U.S. Pat. No. 4,018,827 describes a procedure in which 1,2-cyclohexanedione is prepared by treating cyclohexanone with potassium t-butoxide in the presence of oxygen.

Each of these procedures suffers from disadvantages which limits its utility. Such disadvantages include, the need for dangerous and expensive reagents, which require special handling and expensive equipment, low yields and the like.

The oxazoline compounds of this invention can also be reacted with an equimolar amount, or with a two molar excess of hydroxyl amine in the liquid phase in the presence of hydrogen ions (H+) to provide respectively, a cycloalkane-1,2-dione monoxime and cycloalkanone compounds of the formulas:

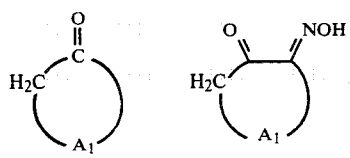

and a cycloalkane-1,2-dione dioxime and cycloalkanone of the formula:

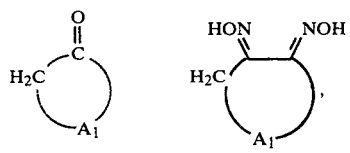

wherein "A" or "$A_1$" are as described above.

The cycloalkane-1,2-dione monoxime and dioxime compounds prepared in accordance with this invention have many uses in commercial applications. For example, the 1,2-cyclohexanedione dioxime is useful as a chelating agent in the extraction of metals, such as cobalt, nickel, palladium molybdenum, and uranium; as an inhibitor of steel corrosion; as a luster agent in cadmium electroplating baths and the like. The monoxime compounds are useful as intermediates in the preparation of d,l-lysine.

DESCRIPTION OF THE PREFERRED EMBODIMENTS

The oxazoline compounds of this invention can e depicted by the following structural formula:

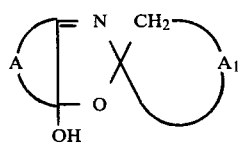

wherein "A" and "$A_1$" are as described above. Compounds which are representatives of such compounds are illustrated by those in which "A" and "$A_1$" complete ring structures derived from the following cycloalkanone compounds:

Cyclopentanone ring structure of the formula:

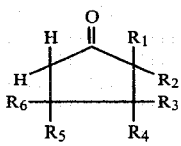

Cyclohexanone ring structure or the formula:

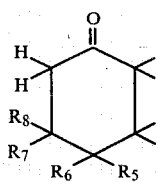

Cycloheptanone ring structure of the formula:

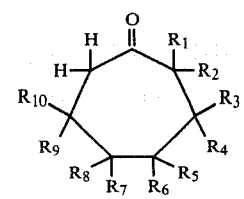

Cycloctanone compounds of the formula:

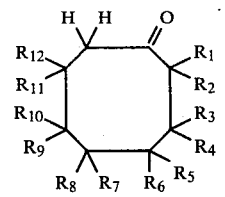

In the above generic formulas, $R_1$ through $R_{12}$, are the same or different and are selected from the group consisting of hydrogen, and an "inert substituent", as defined hereinabove. Illustrative of useful and preferred inert substituents are lower alkyl groups i.e. alkyl having from 1 to 6 carbon atoms, such as methyl, ethyl, propyl, butyl pentyl, hexyl and isomeric forms thereof; lower alkoxy, i.e. alkoxy having from 1 to 6 carbon atoms such as methoxy, ethoxy, propoxy, butoxy, pentoxy, hexyloxy and isomeric forms thereof; nitro; halo, such as chloro, bromo and fluoro; lower alkaryalkyl wherein the alkylmoieties includes from about 2 to about 8 carbon atoms; alkoxyalkyl having from 2 to 6 carbon atoms, such as methoxymethyl, ethoxymethyl, methoxyethyl, propoxymethyl and the like; haloalkyl having from about 1 to 6 carbon atoms, as for example trifluoromethyl phenyl; alkylphenyl having from about 7 to about 12 carbon atoms; lower, alkanoyl, having from about 2 to about 6 carbon atoms, such as acetyl; hydroxy; lower mono- or dialkylaminoalkyl having from 2 to 7 carbon atoms, such as dimethylaminomethyl; lower alkylidenes, having up to 6 carbon atoms such as ethylidene, and butylidene; benzylidene; amino, and di-and monoalkylamino having up to 6 carbon atoms; and like "inert substituents". It should be appreciated that the above listing of "inert substituents" is not intended to be exhaustive of suitable "inert substituents", but is merely intended to be illustrative of useful substituents to enable one of skill in the art to practice the entire invention without undue experimentation. It should be appreciated that the above cycloalkanone compounds which form the moiety which includes A and A, the carbon atoms alpha to the keto function will be substituted with hydrogens.

The preferred embodiments of this invention are symmetrical compounds derived from the aforementioned cycloalkanone compounds wherein:

$R_1$ to $R_{12}$ are individually hydrogen, isopropyl methyl, propyl, ethyl, methoxy, ethoxy, chloro, bromo, fluoro, amino, acetyl, butylidene, benzylidene, ethylidene, or dimethylaminomethyl and no more than six, and more preferably no more than three of said $R_1$ to $R_{12}$ groups are other than hydrogen; and A and $A_1$ are the same.

In the particularly preferred embodiments of this invention:

A and $A_1$ are the same; and any two $R_1$ to $R_{12}$ groups are methyl, ethyl, chloro, fluoro, bromo, phenyl, methoxy or ethoxy, the remainder being hudrogen.

The oxazoline compounds of this invention can be prepared in accordance with the process of this invention as depicted in the following Reaction Scheme A;

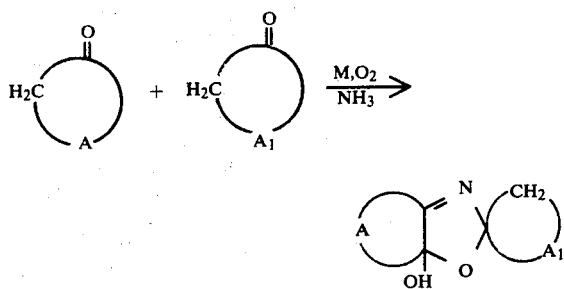

wherein "A"$_1$ and "A" are as described hereinabove and M is a transition metal cation catalyst. It should be appreciated that the above reaction scheme is only intended to depict a gross or overall scheme, because there are possibly various other equilibria involved under the reaction conditions which are intended to be employed in the compound of the process of this invention.

In carrying out the reaction of the above reaction scheme, preferably stoichiometric amounts of the cycloalkanone compound, ammonia, and oxygen are contacted preferably in a "suitable inert solvent" in the pressure of a "catalytically effective" amount of a suitable metal catalyst. While the scheme does depict stiochiometric amounts of the reactants, it should be appreciated that excesses of one or more of the various reactants can be employed. Excesses of the gaseous reactants do not adversely affect the reaction and the isolation of the final product product in relatively pure form, because these excesses are easily disposed of through gaseous evolution. However, in those instances where one or more of the reactants are solids or liquids, an excess of these reactants may adversely affect the isolation of the final product is relatively pure form because of potential problems in separating the product from the unreacted reactant(s).

The manner in which the reactants are contacted is not critical. Accordingly, the reactants, catalyst and reaction solvent can be contacted in any order, order of addition also not being critical. Normally, however, the cycloalkanone compound ammonia and catalyst are added to a solvent, into which oxygen, preferably alone, but also in combination with other inert gases, such as nitrogen, helium, argon, and neon has been added. The addition of oxygen to the solvent is continued throughout and after the addition of the other reactants. The oxygen can be added merely by exposing the reaction mixture to the open atmosphere, or more elaborate procedures may be employed. For example, the oxygen can be bubbled into the mixture contained in an appropriate closed vessel in which an oxygen atmosphere can be maintained. Oxygen uptake can also be measured by a buret. Such a procedure would allow the course of the reaction to be monitored. Also, the addition of oxygen can be carried out with agitation, as for example with a magnetic or mechanical stirrer. Stirring increases the solvation of oxygen and ammonia, and accordingly the rate of reaction.

The ammonia can be added to the reaction mixture directly from the gaseous phase, as for example through the use of a bubbler in much the same manner as the addition of the oxygen. The ammonia can also be added in the form of a pre-formed solution, in which the desired quantity of ammonia has been dissolved beforehand.

Cycloalkanone compounds which are useful as intermediates in the conduct of the process of this invention are those which correspond to the appropriate substrate of the desired oxazoline compounds of this invention. The chemical structure of useful cycloalkanone compounds is apparent from the discussion of the oxazoline compounds of this invention, and they correspond to the following structural formulas:

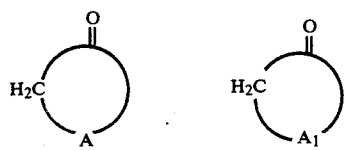

wherein "A" and "$A_1$" are as described above. In the preferred embodiments of this invention, such compounds are cyclopentanone, cyclohexanone, cycloheptanone and cyclooctanone compounds, either unsubstituted or substituted at 1,2, or 3 ring positions with one or more alkyl or alkoxy groups having from about 1 to about 4 carbon atoms halo or phenyl groups. Illustrative of compounds falling within the scope of the above generic description are cyclohexanone; 3-butylcyclohexanone; cyclooctanone; 3,4,5-trimethyl cyclohexanone; 6,7-dimethyl cyclooctanone; 4-methylcyclohexanone; 3,7-dimethylicycloheptanone; 3,4-dimethylcyclohexanone, 4-butylcyclopentanone; 3-isopropylcycloheptanone, 6-isobutylcyclooctanone; -(butylidene)cyclohexanone, 3,4-dichlorocyclohexanone; 3,4-(dibenzylidene)cyclohexanone; 3,4-dibromocyclohexanone; 3-methylcyclohexanone; 3,4-dimethylcyclohexanone; 3-(dimethylaminomethyl) cyclohexanone; 5-(ethylidene)cyclohexanone; 3-amino-4-methylcycloheptanone, 3-isopropylcyclohexanone; 3-methylcyclohexanone; 4-methylcyclohexanone; 3-propylcyclohexanone; 5-methylcyclopentanone; 3-methylcyclopentanone; 4-aminocycloheptanone; 3-bromo-3-methylcycloheptanone, 2-amino-4-isopropylcycloheptanone; 5-methoxycycloheptanone and like compounds. Unsubstituted cycloalkanone compounds, such as cyclohexanone, cycloheptanone, cyclopentanone and cycloctanone are preferred, and cyclohexanone is particularly preferred as a reactant in the process of this invention. As will be apparent from the examples set forth hereinbelow, when cyclohexanone is employed as the cycloalkanone reactant outstanding yields of the desired oxazoline compound can be obtained with appropriate manipulation of reaction parameters. Further the resulting oxazoline compound is useful in preparing extremely useful 1,2-cyclohexanedione, 1,2-cyclohexanedione monoxime and 1,2-cyclohexananedione dioxime.

Cycloalkanone compounds which are useful as intermediates in the practice of this invention can be obtained from a number of sources. Such compounds can be obtained from commercial sources. For example, cyclohexanone, cyclopentanone, cyclotanone and cycloheptanone are commercially available from Aldrich Chemical Company.

The aforementioned compounds, and other useful cycloalkanone compounds can be prepared in accorddance with known preparative procedures. For example, various substituted and unsubstituted cyclohexanone, cyclopentanone, cycloheptanone and cyclocatanone precursors can be prepared in accordance with procedures described in detail in Migrdichian, Vartkes, "Organic Synthesis", Vols. 1 and 2, Reinhold Publishing Corporation, New York (1957).

The process of this invention is carried out in the presence of an "effective metal salt catalyst." As defined herein, "effective metal salt catalyst" is a metal catalyst which is effective for initiating or catalyzing the reaction. It is believed that the catalyst functions as a solvated cation in the reaction solvent. The catalytic caption can exist in the "free form", ie as the solvated cation or it can exist in other forms wherein the cation is complexed with an organic solvent in adduct form or as a complex with a chelating agent for said cation. For example, it is believed that the catalyst cation can exist as an etherate, being complexed with one mole of diethyl ether per mole of composition. The catalyst compositions can also form adducts with aromatic hydrocarbons, such as naphthalene and toluene and chelates with cation chelating agents, such as pyridine, dipyridyl, hexacyclen, the nitrogen analog of 18-crown-6-crown ether; tertiary amines, such as N,N,N,N''-tetramethylethylenedramine; crown ethers, e.g., 15-crown 5 18-crown-6, cryptates, which are bicyclic nitrogen bridged diamines having oxyethylene bridges,w such as 2.2.2-crypt, the ammonia reactant and the like. Adducts and chelates of the catalytic compositions, in some cases may display better crystalline properties than the free-form composition, and therefore may be more convenient for handling and operability. In addition, the chelated cation may significantly influence the catalytic activity during the reaction due to marked differences in ionpairng phenomena. Also chelating agents increase the solubility of the catalyst which usually results in accelerated rates of reaction. However, for purposes of this invention, the free-form catalytic composition and adducts and chelates thereof, are considered to be equivalents as compositions and within the scope of applicable catalytic compositions.

It is not necessary that all of the catalyst be in solution, i.e. as free metal cations and adducts and chelates thereof, at the beginning of the reaction, provided that at least a "catalytically effective amount" is present in solution. As defined herein, "a catalytically effective amount" refers to an amount of the catalyst sufficient under the reaction conditions, i.e. pressure, temperature, solvent, etc., to initiate the reaction. In the preferred embodiments of this invention, the reaction can be initiated by as little as 0.01 mole percent of the catalyst based on the total weight of the cycloalkanone reactant. In the particularly preferred embodiments of this invention, the quantity of catalyst employed is at least 1 mole percent base on the total weight of the cycloalkanone reactant. Larger quantities of catalysts do not appear to adversely affect the reaction. However, because of the high cost of certain useful catalyst, their use is limited by economics.

Catalysts which can be employed in the process of this invention are metal salts which are sufficiently soluble in the reaction solvent under the reaction conditions employed so as to provide a "catalytically effective amount" of the catalyst in solution in the free form or as adducts and chelates thereof, and which are effective to catalyst or initiate the reaction. Preferred catalyst are salts of the transition metals. Illustrative of such salts are the acetate, octanoate, stearate, sulfate, nitrate, halide, hydroxide, phosphate, carbonate, oxide and like salts of transition metals such as copper, iron, nickel, cobalt, platinum, and palladium. These salts may be in the hydrated form or in the anhydrous form. While the above mentioned salts generally are utilizable under the appropriate reaction conditions to form the desired oxazoline compound, as is usually the case in any large group or class, one or more members of the sub-group or sub-class, for one reason or another, are particularly preferred, compared to the class as a whole. In the instant case the particular catalyst preferred for use under the preferred reaction conditions include the cupric salts of aliphatic or aromatic carboxylic acids such as cupric acetate, cupric octanoate, cupric stearate, and cupric naphthalate, as well as, the cupric salts of mineral acids such as cupric chloride, cupric bromide, cupric nitrate and cupric sulfate.

Although the use of a reaction solvent in the process of this invention is not essential, particularly where the cycloalkanone reactant is liquid under the reaction conditions employed, an inert solvent is advantageously employed to facilitate contact between the reactants. The novel process of this invention can be run most readily in the presence of sufficient inert diluent or solvent to solubilize the reactants and a catalytically effective amount of the catayst. Broadly speaking, any solvent or mixtures of solvents in which the cycloalkanone compound, oxygen, ammonia and a "catalytically effective amount" of the catalyst are soluble, and which is inert under the conditions of the inventive process and which does not otherwise interfere with the reaction can be employed as the reaction solvent. Illustrative of such solvents are hydroxy solvants as for example aliphatic alcohols such as methanol, ethanol, propanol, isopropanol, butanol and the like. Because of their superior solubilizing properties, when the process of this invention is conducted under preferred reaction conditions, methanol and ethanol are the reaction solvants by choice.

Reaction temperatures can be varied over a wide range as desired with the proviso that the reaction temperature should be selected such that the temperature is high enough to allow the reaction to proceed; low enough to prevent degradation of reactants and products; and such to allow solubilization of a sufficient quantity of gaseous oxygen. The reaction temperature may be conveniently varied within the range of from about 0° C. to about 200° C., depending on reaction conditions, reaction solvent, reactants, reaction pressures reaction product and other factors. In the preferred embodiment of this inventions the reaction is carried out at room temperature when employing preferred reaction conditions.

Similarly reaction pressures can be varied over a wide range as desired. For example, the reaction can be conveniently carried out at sub-atmospheric, atmospheric or super atmospheric pressure depending on the reaction conditions employed. However, for convenience the reaction is preferably carried out at autogenous pressure.

It will be apparent that manipulation of reaction temperatures and reaction pressures, and reaction solvents within the above described ranges can be carried out to maximize the rate and completeness of reaction and solubility of reactants. For example with a given cycloalkanone reactant and solvent, increased reaction temperature, i.e., above room temperature, will increase reaction rates and solvation of the catalyst, but will decrease the amount of solvated gaseous oxygen reactant. The result could be an overall decrease in the rate of reaction. Conversely, decreased reaction temperature, i.e. below room temperature, will decrease reaction rates and may adversely effect the solvation of the catalyst and solid reactants, while not affecting the degree to which oxygen is solubilized. Accordingly, in the practice of the preferred embodiments of this invention reaction pressures, temperatures and solvents will be manipulated as is necessary to obtain the best results. Usually when reaction temperatures are raised above room temparature for such purposes, as for example increasing the solubility of the solid reactants and catalyst, the reaction pressure is also increased to maintain a sufficient quantity of the gaseous reactants in solution. Conversely, when the reaction temperatures are lowered, the reaction pressure will also be lowered.

It is readily apparent that such manipulation of reaction temperature and pressure greatly broadens the range of useful reaction solvents. When the reaction is conducted in a solvent in which the catalyst and solid reactants are soluble, but gaseous oxygen is insoluble the reaction pressure can be increased until a sufficient quantity of oxygen has been solvated. Similarly, where the catalyst, solid reactants and gaseous reactants are insoluble at room temperature, or where the catalyst and solid reactant alone are insoluble at that temperature both reaction temperature and pressure can be increased until sufficient catalyst, solid reactant and gaseous reactant has been solvated.

The reaction is preferably conducted for a period time sufficient to provide the desired product. Reaction times are not critical and can be varied over a wide range as desired. Usually reaction times will depend on factors such as reaction conditions, i.e., reaction pressures and temperatures, reactants, solvents, catalysts and other factors known to those of skill in the art. Ordinarily the reaction times of up to 24 hours and more can be employed. In most instances, reaction times will vary from in the range of from about 4 hours to about 24 hours under preferred reactions, and these reaction times represent the preferred range of reaction times.

The process of this invention is ordinarily performed as follows: A conveniently sized reactor fitted with an oxygen gas inlet or bubbler and stirring means is charged with a suitable solvent, such as methanol; a catalytically effective amount of a catalyst such as cupric chloride; a solution of ammonia in a solvent such as methanol; and a cycloalkanone such as cyclohexanone to form a reaction mixture. The reaction mixture is then agitated as oxygen is bubbled into the reaction mixture for a time sufficent to convert the cycloalkanone and ammonia into the desired oxazoline.

Work-up of the product mixture can be as follows, after oxygen uptake has substantially ceased, indicating completion of reaction, bubbling is discontinued. The reaction mixture containing the oxazoline product, the catalyst, the solvent and some unreacted ammonia and cycloalkanone is strip of volatiles and the residue taken up in ether. The ether solution is evaporated to dryness to provide the oxazoline reaction product. The oxazoline reaction product can be used as obtained, or further purified employing conventional purification techniques, such as distillation, solvent extraction, recrystallization and the like.

The oxazoline compound of this invention can also be prepared in accordance with the following Reaction Scheme B.

Reaction Scheme B

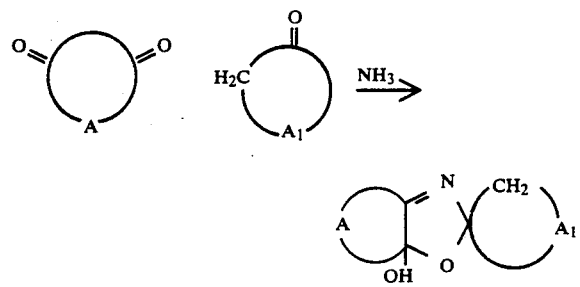

In the above Reaction Scheme B "A" and "A₁" are as described above.

In the above Reaction Scheme B, one moles of the cycloalkane-1,2-dione and one mole of the cycloalkanone are reacted with one mole of ammonia in a suitable inert solvent as for example water, methanol, ethanol and the like. Reaction temperatures and pressures are not critical, and for convenience the reaction is carried out at room temperature and autogenous pressure.

The oxazaline compounds of this invention can be used as intermediates in the preparation of 1,2-cycloalkanedione, 1,2-cycloalkanedione monoxime and 1,2-cycloalkanedione dioxime compounds as depicted in the following Reaction Schemes C, D and E:

Reaction Scheme C

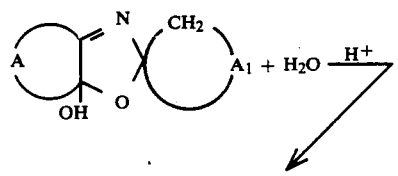

-continued

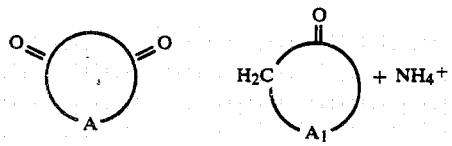

Reaction Scheme D

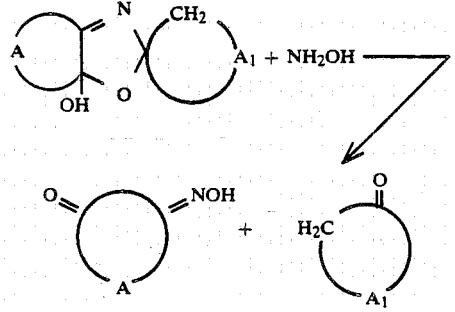

Reaction Scheme E

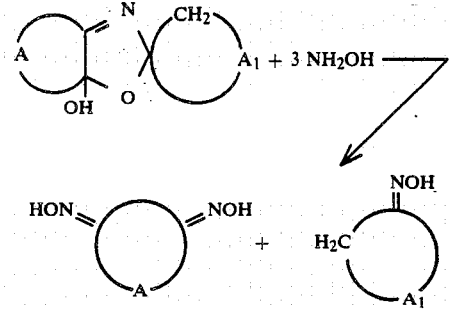

In the above reaction scheme "A" and "A₁" are as described above.

In the reaction of Reaction Scheme C, the oxazoline compound is reacted with water, and in Reaction Schemes D and E with hydroxyl amine, respectively, in the presence of hydrogen ions (H+). The hydrogen ions are introduced into the reaction mixture by solubilizing an appropriate acid. The type of acid employed is not critical. In the instant case, the preferred acids include strong aliphatic and aromatic acids, such as acetic acid, toluenesulfonic acid, and the like, as well as strong mineral acids such as sulfuric acid, phosphoric acid, nitric acid, hydrochloric acid and the like.

The reactions are preferably conducted in an inert reaction solvent which is inert to the reaction conditions, and which possess adequate solvating ability for the reactants. In the reaction of reaction scheme B, the water reactant functions as the reaction solvent, while in the reaction of reaction schemes C and D an inert solvent such as methylene chloride, methanol benzene, xylene, dioxane, carbon tetrachloride and the like. The preferred solvent is water either alone or in combination with a water soluble solvent.

Reaction temperatures and pressures are not critical and can be varied widely as desired. The reactions can be conveniently carried out at a temperature within the range of from about 0° C. to 100° C. However, they are preferably carried out at room temperature. The reactions can be conveniently carried out at sub-atmospheric, atmospheric or super-atmospheric pressure. However, for convenience the reactions are carried out at autogeneous pressure.

The following specific examples are presented to more particularly illustrate the invention and should not be onstrued as being limitations on the scope and spirit of the instant invention.

EXAMPLE I

The Preparation of 4,5,6,7-Tetrahydro-7a-hydroxy spiro benzoxazoline-2',1-cyclohexane A solution of 2 ml of ammonia in 50 ml of anhydrous methanol was added to a round bottom flask fitted with a gas inlet tube and a mechanical stirrer. Fitted to the gas inlet tube was an oxygen buret graduate in milliliters and containing oxygen gas. To this solution was added with stirring 0.1 g of $CuCl_2.H_2O$ and 1.0 g of cyclohexanone. Stirring was continued until all solids had dissolved forming a solution having a blue color. A steady stream of oxygen was bubbled into the solution for approximately nine hours, during which time the solution turned black. Total oxygen uptake was 229 ml. The reaction mixture was extracted with ether and the ether layer concentrated to provide a brown solid. Infra red analysis of tne solid indicated the presence of

function (1690 cm$^{-1}$) and —OH functions, but no keto function. These observations along with $^{13}$C NMR, $^1$H NMR and mass spectral data confirm the conversion of the cyclohexanone into the desired oxazoline compound.

EXAMPLE II

The Preparation of 4,5,6,7-Tetrahydro-7a-hydroxy spiro benzoxazoline-2',1-cyclohexane A solution of 2 ml of ammonia in 50 ml of anhydrous methanol was added to a round bottom flask fitted with a gas inlet tube and a mechanical stirrer. Fitted to the gas inlet tube was an oxygen buret graduated in milliliters and containing oxygen gas. To this solution was added with stirring 0.01 g of $CuCl_2. 2H_2O$ and 1 gram of cyclohexanone. Stirring was continued until all solids had dissolved forming a solution having a blue color. A steady stream of oxygen was bubbled into the solution for approximately nine hours. Total oxygen uptake was 178 ml. The methanol was removed on a rotary evaporator and the residue extracted in ether. The ether solution was filtered and the ether removed on a rotary evaporator to provide a brown solid. The reaction product was again dissolved in methanol and refluxed with activated charcoal. The solution was filtered, and the methanol removed by a rotary evaporator to provide a light brown solid. The product was recrystallized from hexane to provide the desired oxasoline compound having a melting point of 152°-54° C.

Analysis: NMR: One large broad peak at 1.65§ (4H); small peak at 2.5§ (1H); and small peak at 3.4§ (1H) which exchanged with dueterium. IR: Peak at 1690 cm$^{-1}$, (—C≡N—) GLC: Peak at 160° (GV-1).

EXHAMPLE III

The Preparation of 4,5,6,7-Tetrahydro-7a-hydroxy spiro benzoxazoline-2:cyclohexane A solution of 2 ml of ammonia in 50 ml of anhydrous methanol was added to a round bottom flask fitted with a gas inlet tube and a mechanical stirrer. Fitted to the gas inlet tube was an oxygen buret graduated in milliliters and containing oxygen gas. To this solution was added with stirring 0.001 g of $CuCl_2.2H_2O$ and 1 g of cyclohexanone. Stirring was continued until all solids had dissolved forming a pale blue solution. A steady stream of oxygen was bubbled into the solution for approximately six hour. Total oxygen uptake was 153 ml. The methanol was removed by a rotary evaporator and the residue extracted in ether, The ether solvant was removed by rotary evaporator to provide an orange solid. The conversion to the desired oxazoline compound was confirmed by GLC analyses which shows a peak at 160° (OV-1).

EXAMPLE IV

The Preparation of 4,5,6,7-Tetrahydro-7a-hydroxy spiro benzoxazoline-2',1'-cyclohexane A solution of 5 ml of ammonia in 100 ml of anhydrous methanol was added to a round bottom flask fitted with a gas inlet tube and a mechanical stirrer. Fitted to the gas inlet tube was an oxygen buret graduated in milliliters, and containing oxygen gas. This solution was added with stirring 0.05 g of $CuCl_2.H_2O$ and 5 g of cyclohexanone. Stirring was continued until all solids had dissolved forming a solution having a blue color. A steady stream of oxygen was bubbled into the solution for approximately seven hours. Total oxygen uptake was 835 ml. The reaction mixture was heated with activated charcoal and concentrated to provide a brown solid. The solid was dissolved in ether, filtered and concentrated to provide 2.95 g of a brown solid.

The product was recrystallized from hexane to provide 0.65 grams of a pale brown solid.

Analysis: NMR: One large broad peak at 1.65§ (4H), Small peak at 2.5§ (1H); and small peak at 3.4§ (1H) which exhanged with deuterium. GLC: Peak at 160 (GV-1). IR: Peak at 1690 cm$^{-1}$,

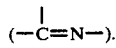

$(-\overset{|}{C}=N-)$.

EXAMPLE V

The Preparation of Cyclohexane-1,2-dione

To a round bottom flask fitted with a mechanical stirrer added 5 ml of $H_2O$ and 0.2 g of the oxazoline product of EXAMPLE I, forming a suspension. To the suspension was added 10 drops of concentrated hydrochloric acid. The suspension was stirred at room temperature for approximately 2 hours afterwhich the water was removed by evaporation. The reaction mixture was extracted with $CH_2Cl_2$ and the resulting solution was dried over anhydrous $MgSO_4$. GLC analyses indicated the presence of cyclohexane-1,2-dione, cyclohexanone and some of the starting oxazoline compound.

EXAMPLE VI

The Preparation of Cyclohexane-1,2-dione

To a round bottom flask fitted with a mechanical stirrer was added a solution of 0.2 g of the product of EXAMPLE I in 5 ml of $CH_2Cl_2$. To the solution was added 1 drop of $H_2SO_4$. The solution was stirred for 2 days at room temperature afterwhich excess acid was neutralized by shaking with $NaHCO_3$. The phases were separated and the $CH_2Cl_2$ liquid phase was dried over anhydrous $Na_2SO_4$. After drying the mixture was concentrated by evaporation to provide the reaction product. over anhydrous $Na_2SO_4$. After drying the mixture was concentrated by evaporation to provide the reaction product NMR analysis indicated the presence of cyclohexane-1,2-dione, cyclohexanone and unreacted starting compound.

EXAMPLE VII

The Preparation of 4,5,6,7-Tetrahydro-7a-hydroxy spiro benzoxazoline-2',1'-cyclohexane A solution of 2 ml of $NH_3$ in 50 ml of ahydrou methanol was charged into a round bottom flask fitted with a gas inlet tube and a mechanical stirrer. Fitted to the gas inlet tube is a source of nitrogen gas. To this solution was added 0.5 g of cyclohexane-1,2-dione, 0.5 g of cyclohexanone and 0.01 g of $CuCl_2.H_2O$ with stirring. Stirring was continued until all solids had dissolved and nitrogen gas was flushed through the system. The reaction mixture was stirred an additional thirty minutes after which the mixture was analyzed by GLC. Analysis indicated the presence of substantial amounts of the above-identified oxazoline compound and small amounts of cyclohexanone. However, no peaks characteristic of cyclohexane-1,2-dione were observed.

EXAMPLE VIII

The Preparation of Oxazoline Compound from Cyclopentanone

A solution of 4 ml of $NH_3$ in 100 ml of methanol was charged into a round bottom flask fitted with a gas inlet tube and a mechanical stirrer. Fitted to the gas inlet tube was an oxygen buret graduated in ml and containing oxygen gas. To this solution was added with stirring 0.03 g of $CuCl_2.2H_2O$ and 1.7 g of cyclopentanone. Stirring was continued until all solids had dissolved forming a solution having a blue color. A steady stream of oxygen was bubbled into the solution for approximately nine hours while the solution was stirred at room temperature. Total oxygen uptake was 295 ml. The methanol reaction solvent was removed by rotary evaporator, and the reaction product eluted through a silica gel column using ethyl acetate. Two fractions were obtained. One fraction showed a nitrile IR peak at 2250 cm$^{-1}$. The other fraction showed $>C=N-$ IR peak at 1685 cm$^{-1}$, and a—OH IR peak at 3100-3400 cm$^{-1}$ which indicated that the reaction mixture contained substantial amounts of the desired oxazoline compound.

EXAMPLE IX

The Preparation of Oxazoline Compound from Cyclopentanone

A solution of 2 ml of $NH_3$ in 50 ml of methanol was charged into a round bottom flask fitted with a gas inlet tube and a mechanical stirrer. Fitted to the gas inlet tube was an oxygen buret graduated in ml and containing oxygen gas. To this solution was added with stirring 0.015 g of CuCl$_2$.2H$_2$O and 1.25 g of cyclooctanone. Stirring was continued until all solids had dissolved forming a solution. A steady stream of oxygen was bubbled into the solution for approximately eleven hours, while the solution was stirred at room temperature. Total oxygen uptake was 145 ml. The methanol reaction solvent was removed by rotary evaporator and the product was extracted in ether. The ether layer was concentrated. IR analysis indicated peaks at 1670 cm$^{-1}$ (>C=N—) and at 3100–3400 cm$^{-1}$ (—OH) which confirmed the presence of the desired oxazoline compound.

COMPARATIVE EXAMPLE I

The Preparation of 1-Cyano-5-Ketohexane

A solution of 2 ml of NH$_3$ in 50 ml of methanol is charged into a round bottom flask fitted with a gas inlet tube and a mechanical stirrer. Fitted to the gas inlet tube was an oxygen buret graduated in ml and containing oxygen gas. To this solution was added with stirring 0.015 g of CuCl$_2$.H$_2$O and 1.1 g of 2-methyl cyclohexanone. Stirring was continued until all solids had dissolved. A steady stream of oxygen was bubbled into the solution for approximately 20 hours, while the solution was stirred at room temperature. Total oxygen uptake was 190 ml. The methanol solvent was removed by rotary evaporator and the product extracted in ether. The ether layer was concentrated. IR analyses confirmed the presence of the desired compound and the lack of the oxazoline compound.

Analysis: IR:

2245 cm$^{-1}$ and (>C=O), 1715 cm$^{-1}$. No —OH peaks were observed.

While certain representative embodiments of the present invention have been shown in detail for the purpose of more particularly illustrating the invention, it will be apparent to those of skill in the art that various changes and modifications can be made herein without departing from the scope and spirit of the invention.

What is claimed is:

1. A process for preparing a compound of the formula:

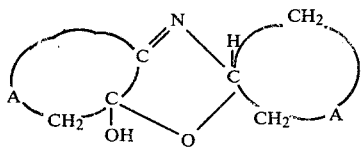

which comprises reacting a compound of the formula:

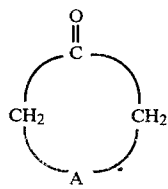

with ammonia and oxygen in the presence of a catalytically effective amount of a catalytically effective transition metal cation, wherein:

A is a straight or branched chain alkylene having from about 3 to about 20 carbon atoms completing a 5, 6, 7 or 8 membered monocyclic ring structure, either unsubstituted or substituted with one or more substituents selected from the group consisting of halo, lower haloalkyl, lower alkyl, lower alkoxy, lower alkylidene, lower phenylalkylidene, amino, lower dialkylamino, and lower alkoxyalkyl.

2. A process according to claim 1 where A is an alkylene chain completing a substituted or unsubstituted 6 membered monocyclic ring structure.

3. A process according to claim 2 wherein A is an alkylene chain completing a 6 membered monocyclic ring structure which is unsubstituted or substituted with up to 3 substituents selected from the group consisting of lower alkyl or lower alkoxy, each having from about 1 to about 6 carbon atoms.

4. A process according to claim 3 wherein said substituents are selected from the group consisting of lower alkyl or lower alkoxy having from about 1 to about 2 carbon atoms.

5. A process according to claim 3 wherein said alkylene chain is unsubstituted.

6. A process according to claim 1 wherein said transition metal cation is selected from cations of metals of the First Transition Series.

7. A process according to claim 6 wherein said transition metal cation is selected from the group consisting of cations of iron, cobalt, nickel and copper.

8. A process according to claim 6 wherein said transition metal cation is cupric cation.

9. A process according to claim 9 wherein said cupric cation is derived from cupric chloride, cupric nitrate, or cupric sulfate.

10. A process according to claim 1 wherein said transition metal cation exhibits a Standard Electrode Potential at 25° C. in 1 mH+ of +.0.153 or greater.

11. A process according to claim 1 wherein said reaction is carried out in an inert solvent.

12. A process according to claim 1 wherein said reaction is carried out at a pressure in excess of 1 atmosphere, and at a temperature of greater than 25° C.

13. A process according to claim 1 wherein the quantity of transition metal cation is at least about 0.01 mole of cation per mole of cycloalkanone compound.

14. A process according to claim 13 wherein said quantity of said transistion metal cation is at least about 1 mole of cation per mole of cycloalkanone compound.

15. A process according to claim 11 wherein said solvent is methanol or ethanol.

16. A process according to claim 5 or 8 wherein said process is conducted in methanol.

17. A process for preparing a compound of the formula

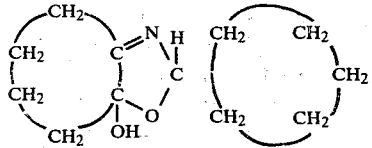

which comprises reacting cyclohexanone with ammonia and oxygen in the presence of a catalytically effective amount of a catalytically effective transition metal cation.

* * * * *